US011968993B2

(12) United States Patent
Schoeppe et al.

(10) Patent No.: US 11,968,993 B2
(45) Date of Patent: Apr. 30, 2024

(54) DOUBLE EMULSIONS (71) Applicant: Cargill, Incorporated, Wayzata, MN (US)

(72) Inventors: Arnulf Schoeppe, Hamburg (DE); Mathieu Balcaen, Ghent (BE); Paul Van Der Meeren, Ghent (BE)

(73) Assignee: Cargill, Incorporated, Wayzata, MN (US)

( * ) Notice: Subject to any disclaimer, the term of this patent is extended or adjusted under 35 U.S.C. 154(b) by 79 days.

(21) Appl. No.: 16/766,502

(22) PCT Filed: Nov. 15, 2018

(86) PCT No.: PCT/US2018/061182
§ 371 (c)(1),
(2) Date: May 22, 2020

(87) PCT Pub. No.: WO2019/103903
PCT Pub. Date: May 31, 2019

(65) Prior Publication Data
US 2020/0375210 A1 Dec. 3, 2020

(30) Foreign Application Priority Data
Nov. 27, 2017 (EP) .................................... 17203842

(51) Int. Cl.
| | | |
|---|---|---|
| *A23D 7/01* | (2006.01) | |
| *A23D 7/015* | (2006.01) | |
| *A61K 8/06* | (2006.01) | |
| *A61K 8/55* | (2006.01) | |
| *A61K 8/60* | (2006.01) | |
| *A61K 8/92* | (2006.01) | |
| *A61K 9/113* | (2006.01) | |
| *A61K 47/24* | (2006.01) | |
| *A61K 47/26* | (2006.01) | |
| *A61K 47/44* | (2017.01) | |

(52) U.S. Cl.
CPC .............. *A23D 7/011* (2013.01); *A23D 7/015* (2013.01); *A61K 8/066* (2013.01); *A61K 8/553* (2013.01); *A61K 8/60* (2013.01); *A61K 8/922* (2013.01); *A61K 8/925* (2013.01); *A61K 9/113* (2013.01); *A61K 47/24* (2013.01); *A61K 47/26* (2013.01); *A61K 47/44* (2013.01)

(58) Field of Classification Search
CPC ........ A61K 47/24; A61K 8/553; A61K 47/26; A61K 47/44; A61K 8/066; A61K 8/60; A61K 8/922; A61K 8/925; A61K 9/113; A23D 7/011; A23D 7/015
See application file for complete search history.

(56) References Cited

U.S. PATENT DOCUMENTS

| | | |
|---|---|---|
| 5,077,077 A | 12/1991 | Suzuki et al. |
| 2009/0029025 A1 | 1/2009 | Pernetti |
| 2010/0233221 A1 | 9/2010 | Folmer |

FOREIGN PATENT DOCUMENTS

| | | |
|---|---|---|
| CN | 104853614 A | 8/2015 |
| EP | 0378893 A2 | 7/1990 |
| EP | 0442831 A1 | 8/1991 |
| EP | 0517987 B1 | 9/1995 |
| EP | 870840 A | 10/1998 |
| EP | 0997075 A1 | 5/2000 |
| EP | 1865786 B2 | 10/2015 |
| JP | s61162148 A | 7/1986 |
| JP | s61174938 A | 8/1986 |
| JP | s63104643 A | 5/1988 |
| JP | 2006504628 A | 2/2006 |
| JP | 2013006882 A | 1/2013 |
| JP | 2016501709 A | 1/2016 |
| JP | 2016503439 A | 2/2016 |
| JP | 2018508222 A | 3/2018 |
| RU | 2472351 C2 | 1/2013 |
| WO | 9738787 W | 10/1997 |
| WO | 03013271 W | 2/2003 |
| WO | 03049553 W | 6/2003 |

(Continued)

OTHER PUBLICATIONS

Akhtar, Mahmood, et al., "Water-in-Oil-in-Water Multiple Emulsions Stabilized by Polymeric and Natural Emulsifiers", Colloids: Fundamentals of Formulation; Special Publication No. 258, Feb. 22, 2001, 133-143.

Aitzetmiiller K., "HPLC and Phospholipids", General Considerations, Fette, Seifen, (1984), vol. 86, pp. 318-322.

Aloisi J.D.; Sherma J.; Fried B., "Comparison of Mobile Phases for Separation and Quantification of Lipids by One-Dimensional TLC and Preadsorbent High Performance Silica Gel Plates", J. Liq. Chromatogr., (1990), vol. 13, pp. 3949-3961.

(Continued)

*Primary Examiner* — Michael B. Pallay (57) ABSTRACT

A water-in-oil-in-water ($W_1/O/W_2$) emulsion comprising a lipid phase (O) and a water phase ($W_2$), the lipid phase being distributed inside the water phase, wherein the lipid phase contains water droplets ($W_1$), wherein the water content inside the lipid phase is between 10 wt % and 80 wt % relative to total weight of the lipid phase, wherein the water droplets are stabilized inside the lipid phase by an emulsifier composition, wherein the emulsifier composition comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is at most 15.5% relative to the total weight of the emulsifier composition and wherein the emulsifier composition has a phospholipid weight ratio R of at most 65%, the ratio R being defined according to Formula R(in %)=100×(PC+PI+PE+PA)/AI.

11 Claims, 3 Drawing Sheets

(56) References Cited

FOREIGN PATENT DOCUMENTS

| WO | 2012059590 A1 | 5/2012 | | |
| WO | WO-2012059590 A1 * | 5/2012 | ............... | A23L 2/58 |
| WO | 2012082065 A1 | 6/2012 | | |
| WO | 2014066623 A1 | 5/2014 | | |
| WO | WO 2014/066632 | 5/2014 | | |
| WO | Wo 2016/0149477 | 9/2016 | | |
| WO | WO-2016149477 A1 * | 9/2016 | ............... | A23D 7/00 |

OTHER PUBLICATIONS

Balcaen, M.; Vermeir, L.; DeClerck, A.; Van Der Meeren, P., "Simple and straightforward determination of the enclosed water vol. fraction of W/O/W double emulsions by analytical photocentrifugation", Particulate Science and Technology, (2016), vol. 34, pp. 565-570.

Lange R.; Fiebig H.J., "Separation of Phospholipids, Standard Methods of DGF", Fett/Lipid, (1999), vol. 101, pp. 77-79.

London E.; Feigenson G.W., "Phosphorous NMR Analysis of Phospholipids in Detergents", J. Lipid Res., (1979), vol. 20, pp. 408-412.

* cited by examiner

DOUBLE EMULSIONS

CROSS REFERENCE TO RELATED APPLICATIONS

This application is a national phase application of PCT/US18/061182, filed 15 Nov. 2018, entitled DOUBLE EMULSIONS, which claims the benefit of priority to European Provisional Application No. 17203842.4, filed 27 Nov. 2017, entitled DOUBLED EMULSIONS, which are hereby incorporated by reference in their entirety.

FIELD OF THE INVENTION

The invention relates to a double water-in-oil-in-water (W/O/W) emulsion, in particular a W/O/W emulsions that include oil droplets containing multiple aqueous droplets, and a method of making the same. The invention further relates to the use of said W/O/W emulsion in making various products, and the various products containing thereof such as food, feed, personal care and pharmaceutical products.

BACKGROUND OF THE INVENTION

A single emulsion is a composition containing a stable mixture of two immiscible phases, in which droplets of one phase are dispersed throughout the other phase. Typical examples of a single emulsion include a water-in-oil (W/O) emulsion and an O/W emulsion.

In the case of a W/O emulsion, a certain content of an aqueous phase (W), e.g. pure water or an aqueous solution, in a form of droplets is uniformly dispersed throughout a lipid content (O), that forms a continuous lipid phase. Lipids, also referred to herein as oils, may include waxes, sterols, fat-soluble vitamins (such as vitamins A, D, E, and K), monoglycerides, diglycerides, triglycerides, phospholipids, fats and others. Examples of lipids suitable for use in the W/O emulsions are disclosed in WO 2014/066632 and include vegetable or animal derived oils, the content thereof varying from 1 to 99 wt %. Single W/O emulsions where the lipid is a fat are typically used to manufacture various food products such as spreads, e.g. margarine.

Single W/O or O/W emulsions can also be used as precursors to prepare double emulsions, e.g. water-in-oil-in-water (W/O/W) emulsions. W/O/W emulsions, also commonly referred to as double emulsions, water-in-oil-in-water double emulsions, or multiple emulsions, are emulsion systems where small water droplets are entrapped within larger oil droplets that in turn are dispersed in a continuous water phase. The advantage of double emulsions is widely recognized in fields as diverse as pharmaceuticals, cosmetics, pest and disease control, food, feed and coatings of the paint type. W/O/W emulsions allow in particular the encapsulation of various active substances in the internal, i.e. inside the oil phase, aqueous phase.

Double emulsions are generally prepared using a 2-step procedure. For W/O/W emulsions, first, a water-in-oil (W/O) emulsion is formed by blending a first (internal) aqueous phase ($W_1$) and an oil phase (O) together in the presence of a suitable oil-soluble (e.g. low hydrophilic-lipophilic balance (HLB) number) emulsifier. This emulsifier adsorbs to the surface of the water droplets and forms a protective coating that reduces and/or prevents undesirable coalescence thereof. Furthermore, the oil-soluble emulsifier reduces the interfacial tension between the oil and the water phase, favoring the formation of droplets, and increasing the stability of emulsions. Second, a W/O/W emulsion is formed by blending the W/O emulsion with a second (external) aqueous phase ($W_2$) containing a suitable water-soluble (e.g. high HLB number) emulsifier. This emulsifier adsorbs to the surface of the oil droplets and forms a protective coating that reduces and/or prevents their subsequent coalescence. The water-soluble emulsifier also reduces the interfacial tension between the water and the oil phase, favoring the formation of droplets, and increasing the stability of the double emulsion. The first step is usually carried out in a high-shear device to produce very fine droplets of water in a continuous lipid. The second emulsification step is typically carried out in a low-shear device to avoid rupturing the multiple droplets. WO 2012/059590 relates to a multiple emulsion of the W/O/W type for stabilization of natural coloring agents against changes in pH values, oxidation and light as well as ingredient interactions. Other methods of manufacturing emulsions can be found in EP 442 831; EP 517 987 and WO 97/38787.

Lecithins, in particular those referred to as low-HLB emulsifiers (typically having an HLB below 5), are widely used to produce W/O emulsions but less used in the manufacturing of double emulsions and in particular of W/O/W emulsions. Lecithin is a naturally occurring compound and is a generic term used to designate a mixture of (glycero) phospholipids including inter alia phosphatidylcholine, phosphatidylethanolamine, phosphatidylinositol and phosphatidic acid. Lecithin may be in a form of a liquid in which case the phospholipids are typically dissolved in an oil phase; or it may be in a form of a powder. Since up to date, powerful emulsifiers are used to stabilize W/O/W emulsions, it would be desirable to provide a way of manufacturing stable emulsions using the naturally occurring lecithin. Also it would be highly desirable to increase the water content of the oil droplets of the W/O/W emulsion, which in turn may be used to produce products having a low fat content as well as other advantageous properties.

An object of the present invention may therefore be to provide a W/O/W emulsion comprising lecithin, in particular a low-fat W/O/W emulsion, having optimum stability at low and ambient temperatures and preferably having an increased content of the internal aqueous phase.

SUMMARY OF THE INVENTION

It has been surprisingly found that one or more of the objectives indicated above may be achieved with a water-in-oil-in-water ($W_1$/O/$W_2$) emulsion comprising a lipid phase (O) and a water phase ($W_2$), the lipid phase being distributed inside the water phase, wherein the lipid phase contains a plurality of water droplets ($W_1$), wherein the water content inside the lipid phase is between 10 wt % and 80 wt % relative to the total weight of the lipid phase, wherein the water droplets are stabilized inside the lipid phase by an emulsifier composition, wherein the emulsifier composition comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a phospholipid weight ratio R of at most 65%, the ratio R being defined according to Formula 1:

$$R(\text{in \%}) = 100 \times \frac{PC + PI + PE + PA}{AI}. \quad \text{Formula 1}$$

wherein PC+PI+PE+PA is the sum of the individual weights of the respective constituents of the AI component and AI is the total weight of the AI component.

The inventors observed that the inventive emulsion has an optimum balance between emulsion stability and fat content. Moreover, when used in the manufacturing of various products, it provides said products with excellent properties. The inventors also observed that while being optimally stable, when used in manufacturing food products the inventive emulsion may provide said products with an agreeable mouthfeel.

DESCRIPTION OF THE DRAWINGS

2B shows an overall stability of the inventive emulsion.

DETAILED DESCRIPTION

The invention relates to a water-in-oil-in-water ($W_1$/O/$W_2$) emulsion (hereinafter "the inventive emulsion") comprising a lipid phase (O) and a water phase ($W_2$), the lipid phase being distributed inside the water phase, wherein the lipid phase contains a plurality of water droplets ($W_1$). The water inside the lipid phase is in the form of droplets and in a content of between 10 wt % and 80 wt % relative to the total weight of the lipid phase.

The water droplets are stabilized inside the lipid phase by an emulsifier composition, which comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount of at most 15.5% relative to the total weight of the emulsifier composition and wherein the emulsifier composition is characterized by a phospholipid weight ratio R of at most 65%, the ratio R being defined according to Formula 1:

$$R(\text{in \%}) = 100 \times \frac{PC + PI + PE + PA}{AI}. \quad \text{Formula 1}$$

wherein PC+PI+PE+PA is the sum of the individual weights of the respective constituents of the AI component and AI is the total weight of the AI component.

The emulsifier composition used in accordance with the invention comprises an Acetone-Insoluble (AI) component, which is understood as the component comprising a group of constituents obtained upon mixing the emulsifier composition with acetone, decanting and extracting the acetone in accordance with the method presented herein below in the "Methods for measurement" section. Preferably the AI component is in a weight ratio of at least 40% relative to the total weight of the emulsifier composition, more preferably at least 50%, most preferably at least 60%. Preferably, the AI is at most 80%, more preferably at most 70%. Preferably, the AI component is between 50 and 70 wt % of the total weight of the emulsifier composition.

As used herein, PC, PA, PE and PI are constituents of the emulsifier composition, which are insoluble in acetone and may be commonly referred to as phospholipid fractions. It is herein understood that the individual phospholipid fractions may contain modified and non-modified fractions. Examples of modified phospholipid fractions include hydrolyzed PC, PA, PE and PI, hereinafter denoted as L-PC, L-PA, L-PE and L-PI, respectively. Preferably, the emulsifier composition used in accordance with the invention contains modified phospholipid fractions in a total amount of less than 20 wt %, more preferably less than 15 wt % relative to their non-modified counterparts.

Preferably, the characteristic ratio R of the emulsifier composition contained by the inventive emulsion is at most 63%, more preferably at most 61%, most preferably at most 60%. Preferably, R is between 30% and 63%, more preferably between 40% and 61%, most preferably between 50% and 59%.

Preferably, the amount of PC in the emulsifier composition contained by the inventive emulsion is at most 15.0%, more preferably at most 13.0%, even more preferably at most 10.5%, most preferably at most 8.5%. Preferably, said amount of PC is at least 3.0%, more preferably at least 5.0%, even more preferably at least 6.0%, most preferably at least 7.0%. Preferably the amount of PC is between 5.0% and 13.0%, more preferably between 6.0% and 10.0%, most preferably between 7.0% and 8.5%.

Preferably, the PA in the emulsifier composition is in an amount of at most 10%, more preferably at most 6.5%, even more preferably at most 4.5%, yet even more preferably at most 4.0%, yet even more preferably at most 3.5%, most preferably at most 3.0% relative to the total weight of the emulsifier composition. Preferably, said amount of PA is at least 0.1%, more preferably at least 1.0%, even more preferably at least 1.5%, most preferably at least 2.3%.

Preferably, the PE in the emulsifier composition is in an amount of at most 30%, more preferably at most 20%, even more preferably at most 16.8%, yet even more preferably at most 16.5%, most preferably at most 16.3% relative to the total weight of the emulsifier composition. Preferably, said amount of PE is at least 1.0%, more preferably at least 6.0%, even more preferably at least 9.5%, most preferably at least 13%.

Preferably, the emulsifier composition used in accordance with the invention has a ratio $P_1:P_2$ of from 1:1 to 1.7:1; wherein $P_1$ is defined as the weight ratio of phospholipid components according to Formula 2:

$$P_1 = \frac{PC + LPC + PI + PA}{PE}; \quad \text{Formula 2}$$

and $P_2$ is defined as the weight ratio of phospholipid components according to Formula 3:

$$P_2 = \frac{PC + LPC + PI}{PE + PA}. \quad \text{Formula 3}$$

Preferably, $P_1$ is in the range of from 1.20 to 2.60; more preferably in the range from 1.30 to 2.25; most preferably in the range from 1.40 to 1.80. Preferably, $P_2$ is in the range of from 0.60 to 1.60; more preferably in the range from 0.80 to 1.40; most preferably in the range from 1.00 to 1.20. In one embodiment, the emulsifier composition used according to present invention preferably has a phospholipid $P_1$ value in the range of from 1.40 to 1.80 and a $P_2$ value in the range of from 1.03 to 1.18; most preferably in the range from 1.07 to 1.16. It was observed that for such values of $P_1$ and $P_2$, the emulsifying composition had a high emulsifying capacity, with good stabilising properties.

Preferably, the emulsifier composition used in accordance with the invention has a ratio $P_3$ of at most 0.70, more preferably at most 0.60, most preferably at most 0.50, wherein $P_3$ is defined according to Formula 4:

$$P_3 = \frac{PE + PI + PA}{AI}; \qquad \text{Formula 4}$$

Preferably, the ratio $P_3$ is at least 0.10, more preferably at least 0.2, most preferably at least 0.3. Preferably, $P_3$ is between 0.38 and 0.50, more preferably between 0.40 and 0.49, even more preferably between 0.43 and 0.48.

The emulsifier composition used in accordance with the invention stabilizes the inventive emulsion and may influence its organoleptic properties. The amount of emulsifier composition is preferably at least 0.1 wt % based on the total weight of the emulsion, more preferably at least 0.3 wt %, most preferably at least 0.5 wt %. Said amount is preferably at most 20.0 wt %, more preferably at most 15.0 wt %, most preferably at most 10.0 wt %.

Preferably, the amount of emulsifier composition is at least 0.5 wt % relative to the amount of the lipid phase, more preferably at least 1.5 wt %, most preferably at least 2.0 wt %. Said amount is preferably at most 10.0 wt %, more preferably at most 8.0 wt %, most preferably at most 6.0 wt %.

Preferably, the emulsifier composition is used in a liquid form, i.e. said emulsifier composition contains the AI component dispersed in a liquid phase which is soluble in acetone. The liquid phase of the emulsifier composition may contain triglycerides as the main component but may also contain monoglycerides, diglycerides, glycerol, glycolipids and fatty acids.

The emulsifier composition used in accordance with the invention may be produced by a process such as the one disclosed for example in WO 2014/066623 and WO 2014/066632, both disclosures being incorporated herein by reference.

The inventive emulsion contains a lipid phase. The lipid phase may be a mixture of a fat which is liquid (the oil part in the fat phase) and a fat which is solid (usually referred to as hardstock fat) at ambient temperature (about 20° C.). Hardstock fat according to the present invention is defined as a fat that has a solid content at 30° C. (N30) of more than 25 wt %, preferably more than 50 wt %, most preferably more than 80 wt % at said ambient temperature. To determine the solid content of hardstock, the method presented in US 2009/0029025 A1 (paragraphs [0055]-[0063]) may be used.

Preferably, the lipid phase contains a fat which is liquid at ambient temperature and is free of hardstock fat. By free of hardstock fat is herein understood that the content of said fat in the lipid phase is below 5 wt % relative to the mass of said lipid phase, more preferably below 3 wt %, most preferably below 1 wt %.

The lipid phase of the inventive emulsion may thus contain a liquid fat (or liquid oil); a solid fat or a mixture of said liquid fat and said solid fat. The terms 'liquid oil' and 'liquid fat' may be used interchangeably within the context of the present invention. The term 'liquid oil' encompasses both triglyceride oils and diglyceride oils. Examples of the liquid oils that may be used in the present invention include without limitation various modified or unmodified vegetable and animal oils, such as palm oil, avocado oil, mustard oil, flaxseed oil, grape oil, peanut oil, coconut oil, olive oil, thistle oil, grape kernel oil, sesame oil, soybean oil, sunflower oil, linseed oil, cotton oil, rapeseed oil, low erucic rapeseed oil (Canola), corn oil, rice oil, safflower oil, kapok oil, sesame oil, evening primrose oil, fish oil and train (whale) oil and mixtures thereof.

Examples of solid fats include without limitation various modified or unmodified vegetable and animal solid fats, such as butter fat and chocolate fat, e.g. cacao butter, shea butter, sal butter; chicken fat; beef tallow; milk fat; lard and mixtures thereof. The above fats and oils may be modified by subjecting them to various treatments, examples thereof including without limitation hydrogenation, fractionation and/or trans-esterification.

The amount of the lipid phase in the inventive emulsion can vary within broad ranges and depends on the application in which the emulsion is intended to be used. For practical reasons, the amount of the lipid phase is preferably at most 90 wt %, more preferably at most 80 wt %, most preferably at most 70 wt % relative to the total weight of the emulsion. Preferably, the amount of the lipid phase is between 0.1 wt % and 90.0 wt %, more preferably between 0.5 wt % and 80.0 wt %, most preferably between 1.0 wt % and 70.0 wt %.

The lipid phase present in the inventive emulsion is in a form of droplets, distributed inside the aqueous phase ($W_2$), for clarity also referred to as the external water phase. The droplets of the lipid phase (the "lipid droplets") preferably contain a plurality of water droplets ($W_1$) and may have any shape and size.

Preferably, the lipid droplets have a size distribution characterized by a mean diameter $D_{4,3}$ of preferably at most 300 μm, more preferably at most 200 μm, most preferably at most 100 μm. Preferably, said $D_{4,3}$ of fat droplets is from 0.01 μm to 300 μm, more preferably from 0.05 μm to 200 μm, most preferably from 0.1 μm to 100 μm. More preferably, said $D_{4,3}$ of fat droplets is from 0.05 μm to 100 μm, more preferably from 0.10 μm to 75 μm, most preferably from 0.15 μm to 50 μm.

The water droplets ($W_1$) preferably have an average combined volume of at least 10% of the volume of the lipid droplet containing said water droplets, more preferably at least 15%, most preferably at least 20%. Said average combined volume is preferably at most 90%, more preferably at most 85%, most preferably at most 80%. By combined volume is herein understood the sum of the individual volumes of the water droplets present in said lipid droplet. By average combined volume is herein understood the average of the combined volumes of water droplets calculated over a number of lipid droplets, preferably at least 50 lipid droplets, more preferably at least 100 lipid droplets, most preferably 500 lipid droplets. It was observed that the average combined volume of water droplets inside the lipid phase of the inventive emulsion may influence its organoleptic properties as well as its functionality.

To aid in homogeneously distributing the water droplets in the lipid phase, said water droplets preferably have a size distribution characterized by a mean diameter $D_{4,3}$ of preferably at most 30 μm, more preferably at most 20 μm, most preferably at most 10 μm. Preferably, said $D_{4,3}$ is from 0.01 μm to 30 μm, more preferably from 0.05 μm to 20 μm, most preferably from 0.1 μm to 10 μm.

Preferably, the total water content ($W_1$) inside the lipid phase is between 15 wt % and 75 wt % relative to the total weight of the lipid phase, more preferably between 20 wt % and 70 wt %, most preferably between 25 wt % and 65 wt %.

The inventive emulsion also contains an external aqueous phase ($W_2$) which is continuous, i.e. the lipid phase of the inventive emulsion is dispersed as droplets within the continuous water phase. Optionally, a second emulsifier can be used to further stabilize the lipid phase inside the continuous aqueous phase ($W_2$). Preferably, said second emulsifier is a high HLB emulsifier, i.e. with an HLB number of above 7. Preferably, said second emulsifier is chosen from the group of emulsifiers consisting of lecithin containing various compositions of phospholipids (referred herewith simply as lecithin), sorbitan esters, sucrose esters, proteins and complexes of proteins and polysaccharides, carboxymethyl cellulose (CMC) and mixtures thereof. A preferred second emulsifier is CMC or whey protein isolate.

Preferably, said second emulsifier is used in an amount of at least 0.05 wt % relative to the total weight of the inventive emulsion, more preferably at least 0.1 wt %, most preferably at least 0.15 wt %. Said amount is preferably at most 10.0 wt %, more preferably at most 8.0 wt %, most preferably at most 6.0 wt %.

The amount of the external aqueous phase in the inventive emulsion can vary within broad ranges and depends on the application in which the emulsion is intended to be used, e.g. of at most 99.9 wt %, more preferably at most 80 wt %, most preferably at most 70 wt %. Preferably, said amount is between 10 wt % and 99.9 wt %, more preferably between 20 wt % and 90.0 wt %, most preferably between 30 wt % and 80.0 wt %.

Preferably, the inventive emulsion is substantially free of acylglycerol-based emulsifiers, which herein are understood as molecules containing esters formed from glycerol and fatty acids. Particular examples of acylglycerols include without limitation polyglycerol polyricinoleate (PGPR), monoglycerides and diglycerides.

In a first preferred embodiment, the inventive emulsion is substantially free of PGPR. By substantially free is herein understood that the inventive emulsion contains less than 2000 ppm PGPR based on its total weight, even more preferably less than 1000 ppm. Most preferably the inventive emulsion is completely free of PGPR, i.e. the content of PGPR is zero ppm.

In a second preferred embodiment, the inventive emulsion is substantially free of mono- and/or diglycerides, i.e. mono- or di-esters of fatty acids and glycerol. Most preferably, the inventive emulsion is completely free of mono- and diglycerides. "Substantially free" and "completely free" bear herein the same meaning as that defined for PGPR.

In a third preferred embodiment, the inventive emulsion is substantially free, more preferably completely free, of PGPR, monoglycerides and diglycerides.

In a preferred embodiment, the inventive emulsion comprises:
(i) between 10 and about 80 wt % of lipid phase, more preferably between 15 and 75 wt %, most preferably between 20 and 70 wt %, said lipid phase containing water droplets, wherein the water content ($W_1$) inside the lipid phase is between 1 and about 50 wt % of, more preferably between 5 and 40 wt %, most preferably between 10 and 30 wt %, wherein the water droplets are stabilized inside the lipid phase with the emulsifier composition, said lipid phase being dispersed as droplets within the aqueous phase, optionally said lipid phase being stabilized inside the aqueous phase by a second emulsifier, wherein the wt % are calculated relative to the total weight of the double emulsion;
(ii) from 10 to 99.9% by weight of aqueous phase ($W_2$), preferably from 20 wt % to 90 wt %; most preferably from 30 wt % to 80 wt %;
(iii) based on the total weight of the emulsion, from 0.05 to about 10 wt %, preferably between 0.20 and 5 wt %, most preferably between 0.4 and 3 wt % of the emulsifier composition;
(iv) based on the total weight of the emulsion, from 0.01 to about 10 wt %, preferably between 0.05 and 5 wt %, most preferably between 0.1 and 3 wt % of the second emulsifier; and
(v) optionally sweeteners, proteins, taste and flavour components, vitamins, colorants, anti-oxidants, bulking agents, solid structuring agents, viscosity modifiers, in concentrations adding up to 100 wt %.

Preferably, the inventive emulsion further comprises one or more viscosity modifiers. Suitable viscosity modifiers include polysaccharides such as starches and gums, examples of said gums including without limitation gelatin, agar agar, pectin, alginic acid, sodium alginate, potassium alginate, beta-glucans, carrageenan, glucomannan, guar gum, gum ghatti, gum tragacanth, karaya gum, tara gum, fenugreek gum, xanthan, maltodextrins and/or locust bean gum. The term "gums", herein refers to all gum polysaccharides of various origins, e.g. from algae, bacteria or fungi.

The inventive emulsion may further contain solid structuring agent particles. Suitable solid particles may be platelets having a preferred average thickness of between 0.01 and 0.5 µm and agglomerates thereof. Preferably, said platelets are edible lipids. Such particles are known for example from EP 1 865 786. In another embodiment, said solid particles are starch granules, wherein said starch granules or a portion thereof are situated at the interface between the two phases, i.e. the aqueous phase and the fat phase. The starch granules preferably have a small granular size in the range of approximately 0.2-20 µm, preferably 0.2-8 µm, more preferably 0.2-4 µm, most preferably 0.2-1 µm. Preferably, the amount of added starch granules in the inventive emulsion corresponds to approximately 0.005-70 vol % of the total emulsion. The amount of added starch granules is preferably determined by the coverage of a water droplet and coverage should be more than 10%. A method of calculating an optimum amount of starch granules in the inventive emulsion as well as the size of said granules can be found in WO 2012/082065, incorporated herein in its entirety by reference.

The inventive emulsion is optimally stable against coalescence, i.e. the coalescence of water droplets with themselves and with the aqueous phase ($W_2$) is reduced as well as the coalescence of the oil droplets with themselves. Also, Ostwald ripening effects in the inventive emulsions were largely prevented. Preferably, an osmotic agent is used to further minimize Ostwald ripening effects.

The inventive emulsion is desirably stable under storage at temperatures from 1° C. up to ambient temperatures. This storage stability may be determined for example by storing a sample of the product in a plastic container at 4, 6, 10, 15, 20 and 25° C. for up to 20 weeks, more preferably up to 24 weeks, most preferably up to 26 weeks. An unstable emulsion may release in time oil (also known as oiling out) and/or water, effects known as phase separation. The extent of phase separation depends on the storage temperature and storage time. In case of the inventive emulsions, the presence of phase separation was determined after the storage time by visual examination (without the aid of a microscope) of the product's surface. Storage stable products do not show a phase separation (no oiling out/no water release) upon storage at 25° C. for at least 10 weeks, preferably at least 26 weeks.

The inventive emulsions have the advantage that they can be manufactured with practically any known process for making W/O/W emulsions. It was observed that the process for making the inventive emulsions may use standard equipment.

The inventive emulsion is preferably an edible emulsion. In case said edible emulsion contains a solid fat, ideally the solid fat content is chosen such that it melts or dissolves optimally at in-mouth conditions. An important indicator is the temperature at which the inventive emulsion breaks up. Preferably, the inventive emulsion breaks up at in-mouth conditions to provide a good oral response. Furthermore, the overall organoleptic impression is preferably smooth without any perceivable grains as this may result in what is generally known as a 'sandy', 'grainy' and/or 'lumpy' mouthfeel.

The invention also refers to a process for preparing the inventive emulsion, comprising the steps of:
(a) contacting:
  (i) the lipid phase containing the emulsifier composition used in accordance with the invention,
  with
  (ii) a first aqueous phase ($W_1$); and
(b) forming a preliminary emulsion wherein the lipid phase provides a continuous phase and wherein the first aqueous phase ($W_1$) is dispersed as a plurality of water droplets inside the lipid phase.
(c) optionally subjecting the preliminary emulsion to a homogenisation treatment to reduce the size of the plurality of water droplets inside said lipid phase;
(d) provide the second aqueous phase ($W_2$), optionally containing a second emulsifier;
(e) mix the preliminary emulsion with the second aqueous phase ($W_2$) to disperse the lipid phase within said second aqueous phase ($W_2$); and
(f) subject the mix of step e) to a homogenisation treatment to produce the inventive emulsion.

The temperature of the first aqueous phase ($W_1$) and/or the lipid phase may be raised in order to facilitate mixing, e.g. typically between 40 and 80° C., preferably between 55 and 70° C. An osmotic agent may be added to said first aqueous water phase to help reducing Ostwald ripening effects in the enclosed water droplets, in particular during storage. Non-limiting examples of osmotic agents include glucose, salts and polyols, e.g. sucrose, fructose, sugars and artificial sweeteners.

The preliminary emulsion may be formed by mixing the first aqueous phase ($W_1$) and the lipid phase with e.g. an Ultra Turrax mixer, preferably at a temperature between 40 and 80° C., more preferably between 55 and 70° C. Preferably, the preliminary emulsion contains water pockets in a continuous lipid phase, the water pockets preferably having dimensions between 0.5 µm and 300 µm, more preferably between 1.0 µm and 200 µm, most preferably between 1.5 µm and 100 µm.

The preliminary emulsion may be subjected to a homogenisation treatment in order to break the water pockets into a plurality of water droplets.

Homogenisation can be effected by a number of possible methods including, but not limited thereto, high shear treatment, pressure homogenisation, colloidal milling, intensive blending, extrusion, ultrasonic treatment and combinations thereof. Preferably, the homogenisation treatment is a pressure homogenisation treatment. Pressure homogenizers typically comprise a reciprocating plunger or piston-type pump together with a homogenising valve assembly affixed to the discharge end of the homogenizer. Suitable high pressure homogenizers include those manufactured by GEA Niro Soavi (IT).

During the high pressure homogenisation, the preliminary emulsion is subjected to high shear rates as the result of cavitation and turbulence effects. These effects are created by said emulsion entering the homogenizing valve assembly from the pump section of the homogenizer at a high pressure.

Preferably, the homogenisation is high pressure homogenisation carried out at a pressure of at least 200 bar, more preferably at least 500 bar, most preferably at least 800 bar. Preferably said pressure is at most 2500 bar, more preferably at most 2000 bar, most preferably at most 1500 bar. Depending on the particular pressure and the flow rate of the emulsion through the homogenizer, one or more homogenisation passes can be used.

In one embodiment, the preliminary emulsion is homogenised by passing it a single time through the homogeniser. Preferably, the pressure used is between 300 bar and 1500 bar, more preferably between 500 bar and 1250 bar, most preferably between 700 bar and 1000 bar.

In one embodiment, the preliminary emulsion is homogenised by multiple passes through the homogeniser, preferably at least 2 passes, more preferably at least 3 passes.

The preliminary emulsion is mixed with a second aqueous phase ($W_2$) and the mix may be homogenized. For example the mixing may be carried out at low shear rates, e.g. by using an Ultra Turrax mixer at speeds between 3000 and 7000 rpm. The homogenisation may be carried out by high shear mixing, high pressure homogenisation, ultrasonic treatment and the like as enumerated hereinabove. The mixing and homogenisation can be combined in a single step and/or by using a single device or carried out sequentially. The mixing and homogenisation times can vary from a few second to a few minutes, suitable times depending on the homogenisation device being between 1 minute and 5 minutes.

The second aqueous phase ($W_2$) preferably contains a second emulsifier, examples being given above.

The invention also refers to another process for preparing the inventive emulsion, comprising the steps of:
(a) forming a composition by contacting:
  (i) the lipid phase containing the emulsifier composition used in accordance with the invention,
  with
  (ii) an aqueous phase; and
  wherein the lipid phase is phase separated from the aqueous phase;
(b) subjecting the composition to a shearing treatment by using a rotor-stator mixer, wherein the rotor of the mixer is positioned inside the water phase and wherein the mixing speed is adjusted to provide a shearing rate sufficient to obtain droplets of the lipid phase dispersed into the aqueous phase, wherein said lipid droplets have a $D_{4,3}$ of preferably at most 300 µm, more preferably at most 200 µm, most preferably at most 100 µm.

Preferably, said $D_{4,3}$ of fat droplets is from 0.01 µm to 300 µm, more preferably from 0.05 µm to 200 µm, most preferably from 0.1 µm to 100 µm. More preferably, said $D_{4,3}$ of fat droplets is from 0.05 µm to 100 µm, more preferably from 0.10 µm to 75 µm, most preferably from 0.15 µm to 50

μm. The inventors observed that such a process is efficient and requires a reduced number of steps to achieve good results.

The invention further relates to a personal care product containing the inventive emulsion. "Personal care products" mean and comprise any cosmetic, hygienic, toiletry and topical care products including, without limitation, leave-on products (i.e., products that are left on keratinous substrates after application); rinse-off products (i.e., products that are washed or rinsed from keratinous substrates during or within a few minutes of application); shampoos; hair curling and hair straightening products; hair style maintaining and hair conditioning products; lotions and creams for nails, hands, feet, face, scalp and/or body; hair dye; face and body makeup; nail care products; astringents; deodorants; antiperspirants; antiacne; antiaging; depilatories; colognes and perfumes; skin protective creams and lotions (such as sunscreens); skin and body cleansers; skin conditioners; skin toners; skin firming compositions; skin tanning and lightening compositions; liquid soaps; bar soaps; bath products; shaving products; and oral hygiene products (such as toothpastes, oral suspensions, and mouth care products).

The invention relates further to pharmaceutical products comprising the inventive emulsion.

The invention relates further to feed products comprising the inventive emulsion.

The invention further relates to various food products containing the inventive emulsion, examples thereof including dips; sauces, e.g. dressing sauces; toppings; dairy-based products such as yoghurt, milk and cheese products; meat products; beverages; and soups. It was observed that the inventive emulsion had a high versatility allowing using it in a wide variety of applications.

In a preferred embodiment, the emulsifier composition is a composition comprising an Acetone-Insoluble (AI) component containing a Phosphatidyl Choline (PC), a Phosphatidyl Inositol (PI), a Phosphatidyl Ethanolamine (PE) and a Phosphatidic Acid (PA), wherein the amount of the PC is at most 13% relative to the total weight of the composition and wherein the composition is characterized by a weight ratio R of at most 65%, the ratio R being defined according to Formula 1 presented above. Preferably, R of the inventive composition is at most 63%, more preferably at most 61%, most preferably at most 60%. Preferably, R is between 30% and 63%, more preferably between 40% and 61%, most preferably between 50% and 59%. Preferably the AI component is in a weight ratio of at least 40% relative to the total weight of the inventive composition, more preferably at least 50%, most preferably at least 60%. Preferably, the AI is at most 80%, more preferably at most 70%. Preferably, the AI component is between 50 and 70 wt % of the total weight of the inventive composition. The emulsifier composition preferably has a ratio $P_1:P_2$ of from 1:1 to 1.7:1; wherein $P_1$ and $P_2$ are defined above in Formulas 2 and 3, respectively. Preferably, the amount of PC in the inventive composition is at most 13.0%, more preferably at most 12.0%, even more preferably at most 10.5%, most preferably at most 8.5%, most preferably at most 7.5%. Preferably the amount of PC is between 5.0% and 13.0%, more preferably between 6.0% and 10.0%, most preferably between 7.0% and 8.5%. The emulsifier composition of the invention preferably has a ratio $P_3$ as defined in Formula 4 of at most 0.50. Said $P_3$ is preferably between 0.38 and 0.50, more preferably between 0.40 and 0.50. The preferred ranges for PA, PE and for the ratios $P_1$, and $P_2$, defined hereinabove are equally applicable and will not be repeated further herein.

In a preferred embodiment, the emulsifier composition is a composition comprising an Acetone-Insoluble (AI) component containing a Phosphatidyl Inositol (PI), a Phosphatidyl Ethanolamine (PE) and a Phosphatidic Acid (PA), wherein the composition is characterized by a weight ratio $P_3$ as defined in Formula 4 of between 0.45 and 0.50. The preferred ranges for the AI, PA, PE, PI and PC contents and ratios R, $P_1$, and $P_2$ as presented hereinabove are equally suitable for this composition and thus will not be repeated further herein.

The emulsifier compositions used in accordance with the invention may be produced by a process such as the one disclosed for example in WO 2014/066623 and WO 2014/066632 by choosing an optimal extraction process.

The invention further relates to food products, in particular those defined hereinabove, containing the compositions of the invention.

The invention is further presented with the help of the following examples and comparative experiments, without being however limited thereto.

Methods for Measurement

Water droplet size measurement (D4,3) is performed with a low resolution NMR, Maran Ultra spectrometer (Oxford Instruments, UK) operating at a frequency of 23.4 MHz. The samples of about 2.5 gram were filled in 18 mm outer diameter glass NMR-tubes (Oxford Instruments, UK) and their exact mass was carefully noted. The free self-diffusion coefficient of the used enclosed water phase (D) was measured using the DSD script (Oxford Instruments, UK) varying the gradient duration (δ) in ten steps between 0.05 and 2.75 ms while keeping the gradient strength (G) and the diffusion delay (Δ) constant at 0.14 T/m and 200 ms, respectively. The free self-diffusion coefficient of the enclosed water phase was measured in triplicate and equalled $1.202 \pm 0.014 \times 10^{-9}$ m$^2$/s.

Pulsed field gradient-NMR experiments on the W/O-emulsions were performed using the stimulated echo pulse (STE) sequence, which was preceded by an inversion recovery experiment for suppression of the NMR-contribution from the oil phase in the emulsion. The inversion recovery experiment on the lipid phase consisting of HOSO-oil and emulsifier composition led to a τ0 of 52.50 ms, MCT-oil containing 2.5 wt % emulsifier composition gave a τ0 of 67.50 ms while MCT-oil with sunflower or soybean lecithin led to a τ0 of 66.25 and 65.00 ms, respectively. These τ0-values were used in all subsequent measurements. These measurements were performed varying the gradient strength (G) between 0 and 3.17 T/m and using a diffusion delay (Δ) of 60, 120 and 220 ms while keeping the gradient duration (δ) constant at 2.5 ms. To determine the volume weighed average droplet size of the water droplet size distribution in the W/O-emulsions, the Murday Cotts model was fitted to the obtained echo decay signals using the diffusion coefficient as determined for the water phase. As the obtained volume weighed average radius strongly varied as a function of the used diffusion delay, which indicates water diffusion through the lipid phase during the measurement, the actual R43 without exchange (R43,0) was calculated using equation 1 as described by Vermeir et al. (2016). R43=R43,0+√D*A (Equation 1).

Lipid droplet size measurement (D4,3)—The volume weighed average diameters (D43) of the lipid droplets were determined using a Malvern Mastersizer 3000 (Malvern Instruments) with Hydro MV accessory. Hereby the Mie theory was used and the refractive indices were set to 1.53+0.01i for the lipid phase and 1.33 for the continuous aqueous phase. The stirring speed was set to 1500 rpm and sample was added until an obscuration between 10 and 20% was reached. To avoid osmotic effects between the water droplets inside the lipid phase and the external aqueous phase, measurements were performed in 0.2M glucose solution.

Determination of the mass or volume of the water droplets inside the lipid phase—To determine the enclosed water volume fraction, analytical photocentrifugation was conducted at room temperature (using air cooling) with a LUMiFuge 116 instrument (LUM GmbH, Germany). Hereby, the enclosed water volume fraction is calculated by measuring the height of the cream layer during centrifugation and taking into account the amount of oil which was used, as described by Balcaen et al. (Balcaen, M., Vermeir, L., Declerck, A., & Van der Meeren, P. (2016a). Simple and straightforward determination of the enclosed water volume fraction of W/O/W double emulsions by analytical photocentrifugation, *Particulate Science and Technology*, 34, 565-570). Rectangular synthetic cells with 2.2 mm path length were used, filled with about 0.35 mL sample. The light intensity was set to 100%. The enclosed water volume fractions were determined in duplicate after the separation process was complete. Three hours of centrifugation at the maximum speed (3000 rpm; 1142 g) usually sufficed. Only in case soybean lecithin was used as the high-HLB emulsifier, six hours of centrifugation at the latter speed was necessary to obtain a stable height of the cream layer. When the double emulsion droplets were large, a small oil layer emerged on top of the cream layer during centrifugation. Moreover, these large droplets sometimes stuck to the wall of the tube which made the border between cream- and serum layer less steep as compared to the emulsions prepared by Balcaen et al. To overcome the aforementioned problems, the 20% transmission value was used to determine the position of the top and bottom of the cream layer. Moreover, the top of the cream layer was determined after 5 minutes of centrifugation instead of at the end of centrifugation. Because mass ratios were used during the preparation of the double emulsion and analytical photocentrifugation is considering the volumes, the mass ratio needed to be converted to a volume ratio. Therefore, the temperature dependency of the density of the used oil phases as well as enclosed water phase were determined. Using the density at the temperature which is reached during centrifugation it is possible to calculate the volume ratios. Mostly a temperature around 30° C. was reached at the end of centrifugation Density measurement—The density as a function of temperature was measured for the lipid phase and the enclosed water phase using a density meter (DMA 5000M, Anton Paar, Germany) The temperature was varied between 25 and 40° C. whereby density measurements were conducted every 3° C. A linear relation between density and temperature was found for the oil phases ($R^2>0.99$) while a $R^2>0.99$ was found if a second order function was fitted to the density as a function of temperature for the water phase.

Determination of the sensitivity of double emulsions towards dilution—A W/O-emulsion was prepared whereby 0.1 g/L 1,3,6,8-Pyrenetetrasulfonic acid tetrasodium salt hydrate (PTSA), which is a fluorescent marker, was added to the water phase and a lipid phase containing 2.5 wt % emulsifier composition was prepared. Using this W/O-emulsion, a W/O/W-emulsion was prepared (see Example 1). Hereby, 2 wt % WPI was used as the high-HLB emulsifier and the double emulsion was prepared at 17500 rpm.

PTSA was used as a fluorescent marker in the determination of the enclosed water volume fraction in double emulsions. The PTSA concentration was determined using a Cary Eclipse fluorescence spectrophotometer (Varian BV, The Netherlands) and an excitation wavelength of 374 nm while the emission was measured at 404 nm. The excitation and emission slits were set to 5 and 2.5 nm, respectively and an averaging time of 1 second was used. Distilled water was used as the blanc and to prepare the standard series. To determine the sensitivity towards dilution in different solutions, samples of this double emulsion were taken and diluted 1:1 (volume:volume) with following liquids:

(i) Enclosed water phase (0.2M Glucose and 0.02 wt % $NaN_3$);
(ii) External water phase (2 wt % WPI in 0.2M Glucose and 0.02 wt % $NaN_3$)
(iii) Isotonic solution containing Na-Caseinate (2 wt % Na-Caseinate in 0.2M Glucose and 0.02 wt % $NaN_3$)
(iv) Hypotonic solution (Deionized water)
(v) Hypertonic solution (0.4M Glucose)

Samples were taken from this mixtures after 1, 5, 10, 15, 30 and 60 minutes and centrifuged at 10.000 g for 1 minute to separate them into a cream- and serum phase. Afterwards, the serum phase was sampled using a syringe and additionally clarified using a 0.45 µm nylon membrane filter.

The obtained serum phases were diluted twentyfold using distilled water. The concentration of PTSA in this diluted water phase was calculated using the standard curve. Then, the percentage of PTSA which remains enclosed could be calculated. Hereby it is assumed that PTSA is only released by external coalescence (between the W/O- and the O/W-interface). It should be noted that also during preparation of the double emulsion, part of the enclosed PTSA will be released due to external coalescence. In the calculations, the concentration of PTSA in the enclosed water droplets is assumed to be a constant 0.1 g/L PTSA. This implies possible osmotic effects, leading to dilution or concentration of PTSA in the enclosed water droplets, are neglected. Taking into account the aforementioned remarks, equation (2) was used to calculate the percentage of enclosed PTSA at every time point.

$$\text{Enclosed PTSA at time } t (\%) = ((Mi,0 - Me,t)/Mi,0)*100 \quad \text{(Equation 2)}$$

In which: $Mi,0 = Ci,0 Vi,0$, the total amount of PTSA which was used; $Ci,0 = 0.1$ g/L, the PTSA concentration and $Vi,0$, the total volume of enclosed water used to prepare the emulsion. $Me,t = 20*Ce,t*(-Ci,0*(Ve,0+Vd,0)/(20*Ce,t-Ci,0))$, the amount of PTSA in the external water phase at time t; $Ce,t$, the concentration of PTSA measured in the external water phase at time t; $Ve,0$ and $Vd,0$, the volume of external water used to prepare the double emulsion and the volume used to dilute the W/O/W-emulsion during the sensitivity test, respectively.

Acetone insolubles were determined according to Lange R., Fiebig H. J. (1999): Separation of Phospholipids, Standard Methods of DGF, Fett/Lipid 101: 77-79. This method is based on the solubility of lecithin components such as triglycerides, fatty acids, sterols, and other acetone-soluble components, and the insolubility of the phospholipids and glycophospholipids in acetone under the test conditions. The latter are termed acetone insolubles (AI).

AI may also be determined in accordance with AACC International Method 58-35.01—"*Acetone-Insoluble Lecithin*", however the former method is preferred.

Phospholipid Composition: The phospholipid composition, i.e. the amount of PC, PA, PI and PE and their hydrolysed fractions was determined using a liquid-chromatographic method applied on emulsifier compositions having an AI set to 60% relative to the total weight of the emulsifier composition. AI amount can be adjusted by adding (or extracting e.g. with acetone) the necessary amount of the acetone soluble part (mainly triglycerides) of said composition in order to bring the AI amount to 60%. The identification and quantification of the various phospholipid components may conveniently be executed by different methods, including thin-layer chromatography (TLC), high performance liquid chromatography (HPLC) and $^{31}P$ nuclear magnetic resonance spectroscopy ($^{31}P$-NMR) for the phospholipids only. Suitable methods are disclosed in London E., Feigenson G. W. (1979): Phosphorous NMR Analysis of Phospholipids in Detergents, J. Lipid Res. 20: 408-412; Aitzetmüller K. (1984): HPLC and Phospholipids, Part I: General Considerations, Fette, Seifen, Anstrichm. 86: 318-322; and Aloisi J. D., Sherma J., Fried B. (1990): Comparison of Mobile Phases for Separation and Quantification of Lipids by One-Dimensional TLC and Preadsorbent High Performance Silica Gel Plates, J. Liq. Chromatogr. 13:3949-3961.

EXAMPLES AND COMPARATIVE EXPERIMENTS

Examples

An emulsifier composition (EC) obtained also from soybean oil and having a composition as presented in Table, as well as two other commercial lecithins one obtained from soybean (Leciprime) and one obtained from sunflower oil (Topcithin), which were not deoiled, were used. Other used emulsifiers were sodium caseinate (Na-Caseinate; 5.5% moisture; 96% protein on dry matter), whey protein isolate (WPI), carboxymethylcellulose (CMC; Degree of substitution=0.65-0.90; Viscosity 2% solution=1500-3100 mPa·s) and powdered soybean lecithin (Emulpur IP)

As the fat phase, high oleic sunflower oil (Hoso; Iodine Value=87; 82% C18:1) and MCT-oil (Miglyol 812N) with approximately 58% C8:0 and 41% C10:0 were used.

The water phases $W_1$ and $W_2$ contained 0.2M Glucose (VWR Chemicals: BDH Prolabo, 40 Leuven, Belgium), 0.02 wt % of anti-microbial agent NaN3 (Sigma-Aldrich, Steinheim, Germany). Glucose was added as an osmotic agent to reduce Ostwald ripening effects. Glucose was used instead of a salt in order to avoid charge effects. To test the sensitivity of double emulsions towards dilution in different kinds of aqueous solutions, an emulsion containing 0.1 g/L of the fluorescent marker 1,3,6,8-Pyrenetetrasulfonic acid tetrasodium salt hydrate (PTSA; Sigma-Aldrich, Steinheim, Germany) in the enclosed water phase was prepared.

2.5 wt % of EC or Leciprime or Topcitin was added to the oil phase after which this phase was heated to 60° C. An Ultra-Turrax (type 525-10G, IKA®-Werke, Germany) was used to prepare the preliminary W/O-emulsions (30/70, w/w) at 60° C. The water phase was added gradually during stirring after which stirring was continued to obtain the final preliminary emulsion. Afterwards, the preliminary emulsion was processed using 1 pass through a Microfluidizer (type M110S, Microfluidics) operating at 840 bar while the temperature was maintained at 60° C. using a heating bath.

In case MCT-oil was used, the external water phase was mixed at room temperature with freshly prepared preliminary emulsion in a 50/50 (w/w) ratio with an Ultra-Turrax 525-10G (IKA®-Werke, Germany) at 13500, 17500 or 24000 rpm for 3 minutes.

For preliminary emulsions prepared using Hoso as the oil phase, the preparation of a premix was necessary. The premix was prepared by mixing for 1 minute at 6500 rpm using an Ultra-Turrax S25KV-25G-IL (IKA®-Werke, Germany) which is a rotor-stator homogenizer with a larger diameter. Afterwards, mixing could be continued with an Ultra-Turrax 525-10G (IKA®-Werke, 67 Germany) as described previously.

The external water phase only differs from the enclosed water phase in the presence of 2 wt % of either WPI, Na-Caseinate, CMC or powder soybean lecithin. All samples were stored at 5° C. after preparation.

Results

Figure 1:
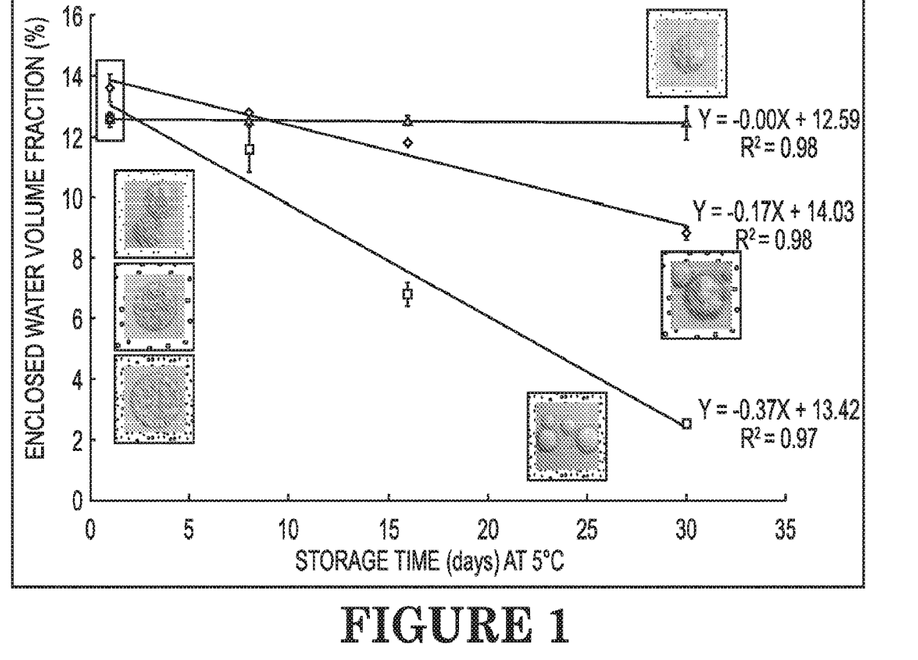
FIG. 1 shows the influence of the emulsifier composition on the enclosed water volume fraction.

FIG. 1 reveals that the EC had a large influence on the enclosed water volume fraction. Indeed, when EC was used, during the 30 days of storage at 5° C., the enclosed water volume fraction decreased with 0.00±0.00%/day while a decrease with 0.17±0.02%/day and 0.37±0.05%/day is calculated for the commercial lecithins, respectively. Therefore, using EC, the highest storage stability could be reached while using sunflower lecithin the storage stability was very low. Finally, using soybean lecithin, an intermediate stability was obtained. As seen on the inset microscopic image of the W/O/W-emulsion prepared using sunflower lecithin and stored for 30 days at 5° C., these emulsions are almost completely devoid of enclosed water (FIG. 1).

Double emulsions were prepared using long chain unsaturated triglyceride oil (Hoso) as the oil phase. EC was used as the low-HLB emulsifier while the high HLB-emulsifier was varied.

Figure 2A:
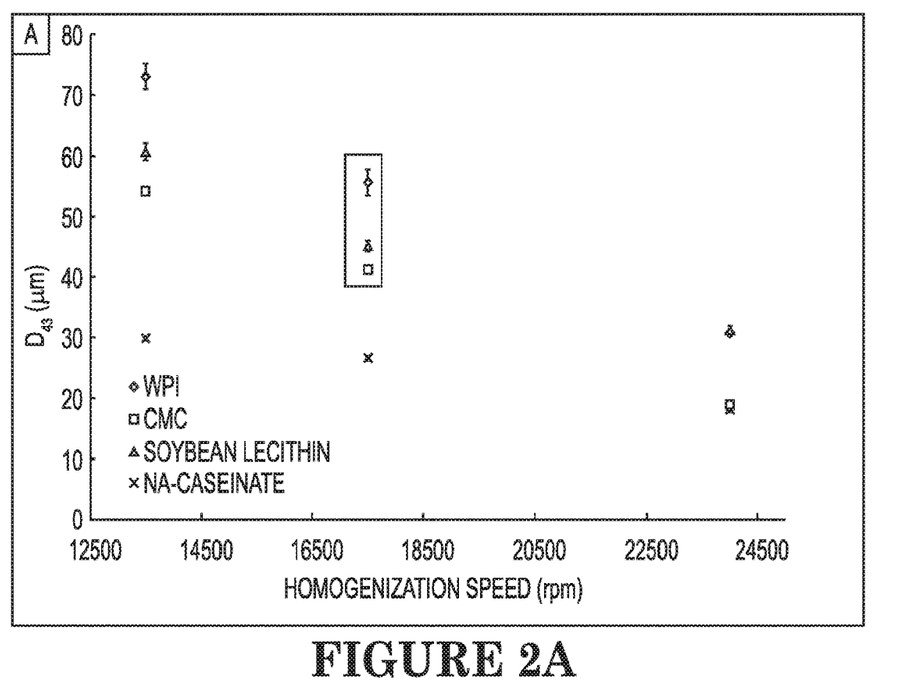
FIG. 2A shows the influence of whey protein isolate on the size of the droplets of the inventive emulsion.

W/O/W-emulsions could be prepared without adding an additional high-HLB emulsifier to the external water phase. FIG. 2A shows that when whey protein isolate is used, the biggest droplets are obtained. The increased viscosity due to the addition of CMC to the external water phase has a beneficial effect during preparation as it reduces the viscosity ratio between dispersed and continuous phase.

Figure 2B:
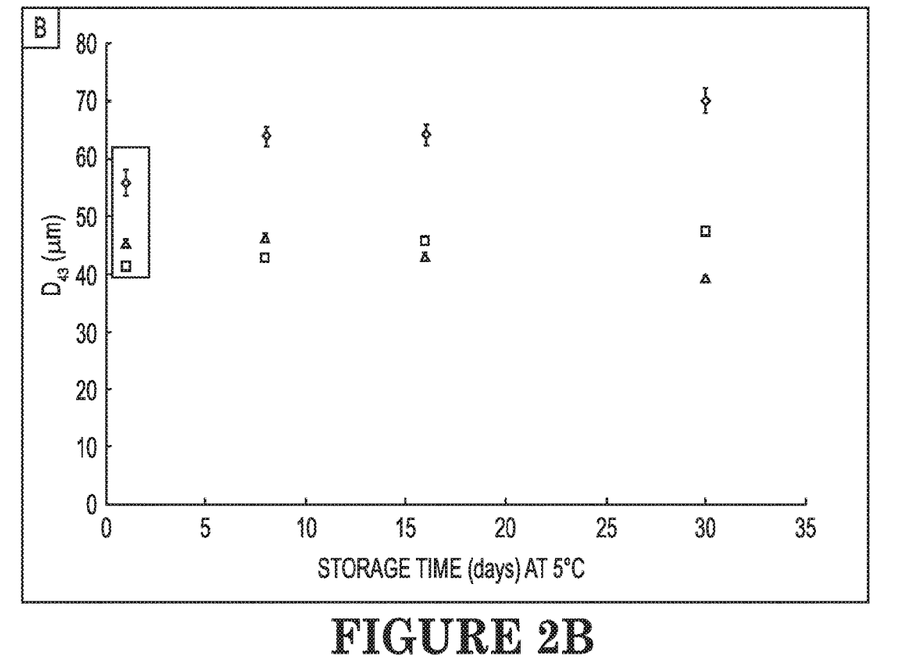

Considering the storage stability of the double emulsion droplet size (FIG. 2B) it can be mentioned that during 30 days of storage at 5° C., the droplet size increased with 14 and 26% for CMC and WPI, respectively. In contrast, when using commercial (soybean) lecithin, the droplet size decreased to 87% of its initial value.

Figure 3:
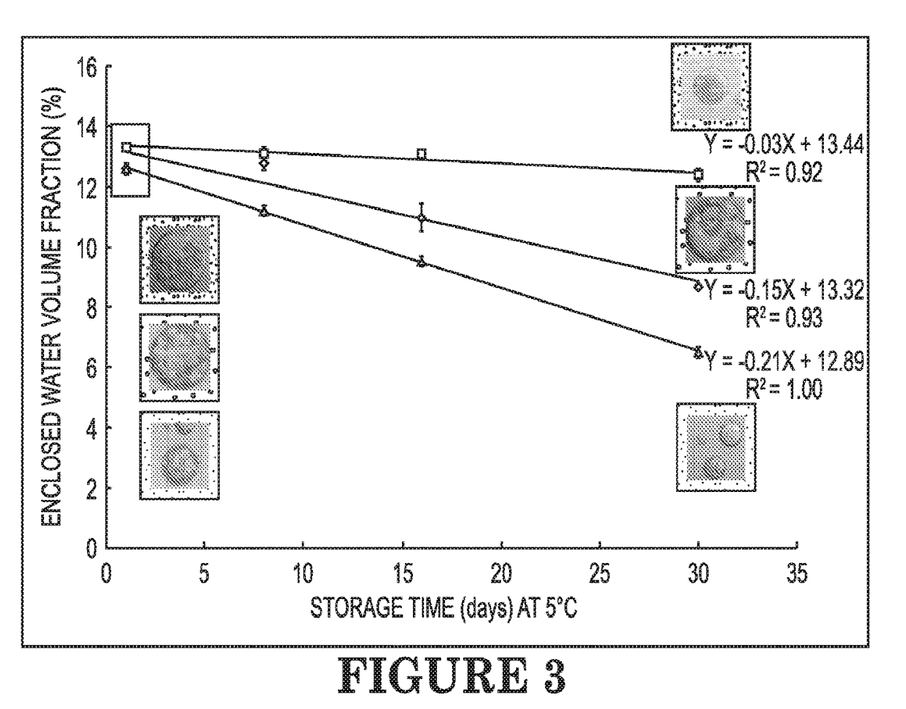
FIG. 3 shows the influence of carboxymethyl cellulose on the storage stability of the inventive emulsion.

Following the enclosed water volume fraction (%) as a function of storage time at 5° C. (FIG. 3) reveals that CMC helps the storage stability of the W/O/W-emulsions. Indeed, the enclosed water volume fraction decreases with 0.15±0.03 and 0.21±0.00%/day when WPI and soybean lecithin are used, respectively. In contrast, a very slow loss of enclosed water volume during storage of 0.03±0.01%/day is noted in case CMC is added to the external water phase.

Because the enclosed water volume fraction was very low when Na-Caseinate was used as high-HLB emulsifier, it was tested whether the W/O/W-emulsions, prepared using EC as low-HLB emulsifier and WPI as high-HLB emulsifier, were sensitive to Na-Caseinate when this compound was added after production of the W/O/W-emulsion. Therefore, the double emulsions were diluted in an isotonic aqueous phase containing Na-Caseinate. In order to be able to compare the results of the aforementioned dilution, the double emulsion was diluted in two other isotonic solutions namely the enclosed water phase itself and the external water phase (containing 2 wt % WPI).

Figure 4:
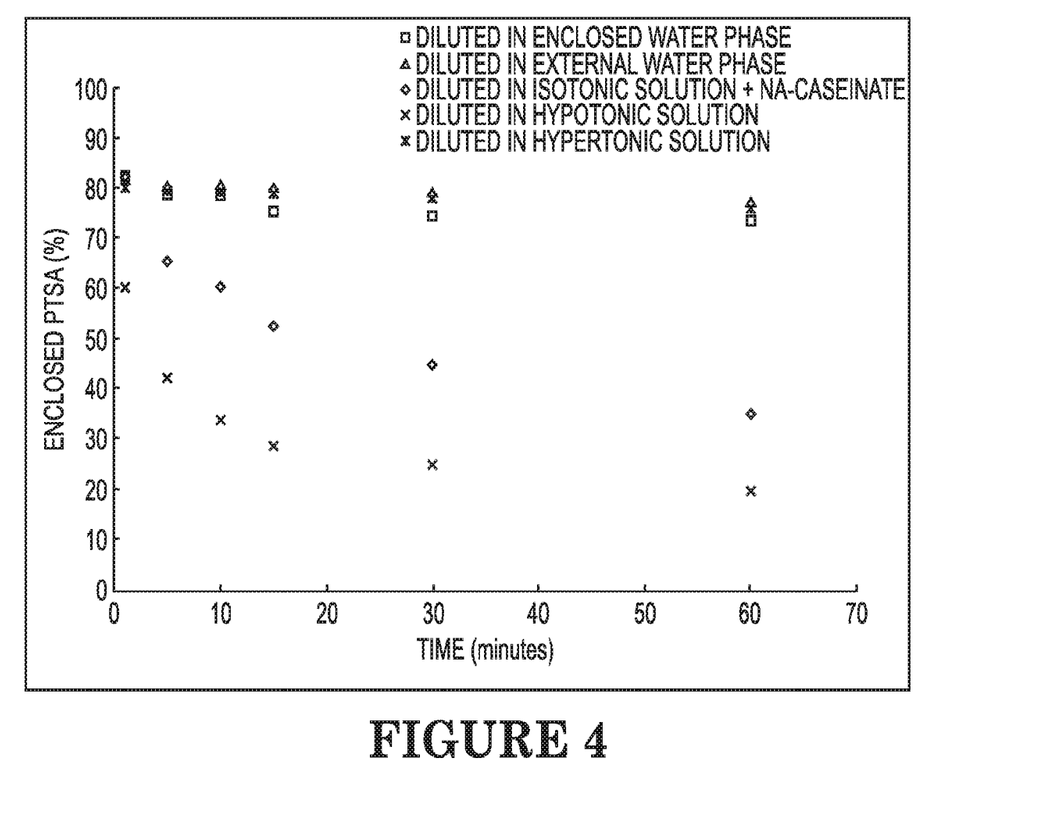
FIG. 4 demonstrates the capability of the inventive emulsion to effectively control the release of various components contained thereby.

The release of a marker (PTSA) due to osmotic gradients between enclosed and external water was used to test the dilution effect. This was tested by dilution of the double emulsion with a hyper-(0.4M glucose) and a hypotonic (distilled water) aqueous phase. FIG. 4 shows that adding a solution of 2 wt % Na-Caseinate in isotonic medium led to the release of enclosed water. This effect was, however, absent if the double emulsion was diluted in the enclosed (isotonic) water phase or in an isotonic water phase containing WPI (external water phase).

These observations have practical implications. Indeed, when controlled release of enclosed compounds is required it is interesting to note that the inventive emulsion enable such effects. This is in particular interesting for pharmaceutical or personal care products where such effects are often desired. The inventive emulsion also enables a food designer to create novel foods wherein the release of certain ingredients or flavours may be controlled.

The invention claimed is:

1. A water-in-oil-in-water ($W_1/O/W_2$) emulsion comprising a lipid phase (O) and a water phase ($W_2$), the lipid phase being distributed inside the water phase, wherein the lipid phase contains a plurality of water droplets ($W_1$), wherein the water content inside the lipid phase is between 10 wt % and 80 wt % relative to the total weight of the lipid phase, wherein the water droplets are stabilized inside the lipid phase by a first emulsifier composition and a second emulsifier composition, the second emulsifier in range of from about 0.1 wt % to about 10 wt % of the emulsion, wherein the first emulsifier composition comprises an Acetone-insoluble (AI) component containing a Phosphatidyl Choline (PC), a Phosphatidyl Inositol (PI), a Phosphatidyl Ethanolamine (PE) and a Phosphatidic Acid (PA), wherein PC is in an amount by weight of at most 15.5% relative to the total weight of the first emulsifier composition and wherein the first emulsifier composition is characterized by a phospholipid weight ratio R of at most 65%, the ratio R being defined according to Formula 1:

$$R(\text{in \%}) = 100 \times \frac{PC + PI + PE + PA}{AI}. \quad \text{Formula 1}$$

wherein:
the water droplets ($W_1$) have an average combined volume of at least 10% of the volume of the lipid droplet containing said water droplets;
PC+PI+PE+PA is the sum of the individual weights of the respective constituents of the AI component and AI is the total weight of the AI component; and
the second emulsifier comprises lecithin, a sorbitan ester, a sucrose ester, a protein, a polysaccharide, a carboxymethyl cellulose, or a mixture thereof.

2. The emulsion of claim 1, wherein R is between 30% and 63%.

3. The emulsion of claim 1, wherein the amount of the first emulsifier composition is at least 0.1 wt % based on the total weight of the emulsion.

4. The emulsion of claim 1, wherein the lipid phase contains a liquid fat or a liquid oil chosen from the group consisting of palm oil, avocado oil, mustard oil, flaxseed oil, grape oil, peanut oil, coconut oil, olive oil, thistle oil, grape kernel oil, sesame oil, soybean oil, sunflower oil, linseed oil, cotton oil, rapeseed oil, low erucic rapeseed oil (Canola), corn oil, rice oil, safflower oil, kapok oil, sesame oil, evening primrose oil, fish oil and train oil and mixtures thereof.

5. The emulsion of claim 1, wherein the amount of the lipid phase is at most 90 wt % relative to the total weight of the emulsion.

6. The emulsion of claim 1, wherein the lipid phase is in the form of lipid droplets having a size distribution characterized by a mean diameter D4,3 of at most 300 μm.

7. The emulsion of claim 1, wherein the water droplets ($W_1$) have a size distribution characterized by a mean diameter $D_{4,3}$ of at most 30 μm.

8. The emulsion of claim 1, further comprising one or more viscosity modifiers.

9. A food, feed, personal care or pharmaceutical product comprising the emulsion of claim 1.

10. The emulsion of claim 1, wherein R is between 40% and 61%.

11. The emulsion of claim 1, wherein R is between 50% and 59%.

* * * * *